United States Patent [19]
Steffan et al.

[11] Patent Number: 5,958,757
[45] Date of Patent: Sep. 28, 1999

[54] BIOLOGICAL CONVERSION OF ORGANIC COMPOUNDS

[75] Inventors: Robert Jon Steffan, Newtown; Kevin Rock McClay, Morrisville, both of Pa.

[73] Assignee: Envirogen, Inc., Lawrenceville, N.J.

[21] Appl. No.: 08/713,992

[22] Filed: Sep. 13, 1996

[51] Int. Cl.[6] ............................... B09B 3/00; C02F 3/34; C12N 1/00

[52] U.S. Cl. ................ 435/262.5; 435/264; 435/170; 435/874; 435/289.1; 570/220; 588/248

[58] Field of Search ........................... 570/220; 585/641; 588/248; 435/243, 252.3, 252.34, 264.84, 289.1, 262.5, 262, 29, 41, 170, 874

[56] References Cited

U.S. PATENT DOCUMENTS

| | | | |
|---|---|---|---|
| 4,853,334 | 8/1989 | Vandenbergh et al. | 435/262 |
| 4,959,315 | 9/1990 | Nelson et al. | 435/167 |
| 5,017,495 | 5/1991 | Yen et al. | 435/320.1 |
| 5,024,949 | 6/1991 | Hegeman et al. | 435/262 |
| 5,071,755 | 12/1991 | Nelson et al. | 435/167 |
| 5,079,166 | 1/1992 | Winter et al. | 435/262 |
| 5,171,684 | 12/1992 | Yen et al. | 435/252.3 |

OTHER PUBLICATIONS

Little, C. D., et al., 1988. *Appl. Environ. Microbiol.* 54:951–956.
Nelson, M. J. K. et al., 1988. *Appl. Environ. Microbiol.* 54:604–606.
Wackett, L. P., and D. T. Gibson. 1988. *Appl. Environ. Microbiol.* 54:1703–1708.
Alvarez–Cohen, L. et al., *Applied Environ. Microbiology*, 57(4), 1031–1037 (1991).
Tsien, H.–C., et al., 1989. *Appl. Environ. Microbiol.* 55:3155–3161.
Fox B. G., et al. 1990. *Biochemistry.* 29:6419–6427.
Brockman, F. J., et al., 1995. *J. Haz. Material.* 41:287–298.
Hazen, T.C. et al., 1994, *In situ Remediation: Scientific Basis for Current and Future Technologies*, Battelle Press, Richmond, WA; pp. 137–150.
Lombard et al., 1994, R.E. Hinchee (ed.) *Air Sparging for Site Remediation*, Lewis Publishers, Boca Raton, FL, pp. 81–96.
Semprini, L., and P. L. McCarty. 1991. *Ground Water* 29:365–374.
Prior, S. D. and H. Dalton. 1985. *J. Gen. Microbiol.* 131:155–163.
Bouwer, E. J., and P. L. McCarty. 1983. *Appl. Environ. Microbiol.* 45:1286–1294.
Mikesell, M. D., and S. A. Boyd. 1990. *Appl. Environ. Microbiol.* 56:1198–1201.
Olsen, R. H.,et al., 1994. *J. Bacteriol.* 176: 3749–3756.
Haigler, B. E., et al., 1992. *Appl. Environ. Microbiol.* 58:2237–2244.
Ensley, B. D. et al., 1983. *Science* 222:167–169.
Ensley, B. 1991. *Ann. Rev. Microbiol.* 45:283–299.
Yen, K. M. and M. R. Karl. 1992. *J. Bacteriol.* 174:7253–7261.
Yen, K.–M., et al., 1991. *J. Bacteriol.* 173:5315–5327.
McClay, K., et al., 1995. *Appl. Environ. Microbiol.* 61: No. 9, pp. 1–3.
Bagley, D. M., and J. M. Gossett. 1995. *Appl. Environ. Microbiol.* 61:3195–3201.
Landa, A. S. et al., 1994. *Appl. Environ. Microbiol.* 60:3368–3374.
Speitel, G. E., et al., 1993. *Water Res.* 27:15–24.
Oldenhuis, R., et al., 1989. *Appl. Environ. Microbiol.* 55:2819–2816.
Henson, J. M., M. V. Yates, and J. Cochran. 1989. *J. Ind. Microbiol.* 4:29–35.
Strand, S. E., and L. Shippert. 1986. *Appl. Environ. Microbiol.* 52:203–205.
Alvarez–Cohen, L, et al., 1992. *Appl. Environ. Microbiol.* 58:1886–1893.
Jahng, D. and T. K. Wood. 1994. *Appl. Environ. Microbiol.* 60: 2473–2482.
Winter, R., et al., 1989. *Bio/Technology.* 7:282–285.
Chang, H–. L., and L. Alvarez–Cohen. 1995, *Biotechnol. Bioeng.* 45:440–449.
Chang, H–. L., and L. Alvarez–Cohen. 1995. *Environ. Sci. Technol.* 29:2357–2367.
Shields, M. S., et al., 1989. *Appl. Environ. Microbiol.* 55: 1624–1629.
Whited, G. et al., *J. Bacteriology*, 173(9), 3010–3016 (1991).
Pavel, H. et al.,*J. Bacteriology*, 176(24), 7550–7557 (1994).
Vogel, T. et al., *Applied Environ. Microbiology*, 49(5), 1080–1083 (1985).
Bouwer, E. et al., 1981. *Environ. Sci. Technol.* 15:596–599.
Stead, D.E. et al., *J. of Applied Bacteriology*, 72:315–321 (1992).
Van Beelen, P. et al., *Hydrobiol. Bull.*, 24:13–21 (1990).
Thompson, I.P. et al., *FEMS MIcrobiol. Ecol.*, 102:75–84 (1993).
Antonio Trilli. 1986. Scale–up fermentations. pp. 277–307 in Arnold L. Demain and Nadine A. Soloman (eds.), "Manual of Industrial Microbiology and Biotechnology." American Society for Microbiology, Washington, D.C.
Marley, M.C., D.J. Hazebrook, and M.T. Walsh. 1992. *Groundwater Monitoring Review* 2:137–145.

(List continued on next page.)

Primary Examiner—Ponnathapura Achutamurthy
Assistant Examiner—P. Ponnaluri
Attorney, Agent, or Firm—Synnestvedt & Lechner LLP

[57] ABSTRACT

Saturated aliphatic halocarbons, including environmental contaminants, are degraded to innocuous, environmentally acceptable compounds by contact, either in situ or in a bioreactor, with microorganisms that produce aromatic oxygenases, preferably with use of a co-substrate, for example, phenol, toluene, benzene, ethylbenzene and xylene, including the provision of novel bacteria that produce aromatic oxygenases, and new recombinant microorganisms that contain cloned aromatic oxygenase genes, examples of saturated aliphatic halocarbon that may be degraded to innocuous compounds being chloroform; bromoform; 1,2-dichloroethane; 1,2-dibromoethane; monochloroethane and monobromoethane.

18 Claims, 1 Drawing Sheet

OTHER PUBLICATIONS

Mackay D. and W.Y. Shiu. 1981. *J. Phys. Chem. Ref. Data* 10:1175–1199.

Herrero, M., et al., 1990. *J. Bacteriol.* 172:6557–6567.

De Lorenzo, V. et al., 1993. *Gene* 123:17–24.

Ensley, B. et al., *Applied Environ. Microbiology*, 60(1), 285–290 (1994).

Whited, G. M., and D. T. Gibson. 1991. J. Bacteriol. 173:3017–3020.

B.D. Ensley and P.R. Kurisko, 1994. *Appl. Environ. Microbiol.* 60:285–290.

Yanisch–Perron, C. et al., 1985. *Gene* 33:103–119.

Welch, D., *Clinical Microbiology Reviews* 4:422–438 (1991).

Alvarez–Cohen, L. and P. L. McCarty. 1991. *Appl. Environ. Microbiol.* 57:228–235.

Egli, C., et al., 1987. *FEMS Microbiol. Lett.* 43:1295–1299.

Wilson, K. 1993. pp. 2.4.1–2.4.5. in F. M. Ausubel, et al., (eds.), *Current Protocols in Molecular Biology*. Current Protocols, Brooklyn, N.Y.

McClay et al., Applied Environmental Microbiology., vol.62., No.8., pp. 2716–2722, Aug. 1996.

Mikesell et al., Applied Environmental Microbiology., vol. 56, No.4., pp. 1198–1201, Apr. 1990.

BIOLOGICAL CONVERSION OF ORGANIC COMPOUNDS

FIELD OF THE INVENTION

This invention relates to a method for converting undesirable materials into acceptable materials. In particular, the present invention relates to a biological method for converting environmental contaminants into environmentally acceptable compounds.

The field of the present invention will be described initially in connection with the contaminant trichloromethane (hereafter referred to as "chloroform" or "CF"). It should be understood that the present invention has applicability to the treatment of other halocarbon contaminants, as will be described below.

Chlorinated solvents, such as chloroform (CF) and trichloroethylene (TCE), are common groundwater contaminants. The contamination is caused primarily by poor disposal practices and leaking storage tanks. Chloroform is used extensively in the production of fluorocarbon-22, which is a refrigerant, and in the production of fluoropolymers. Miscellaneous other uses of chloroform include use as a solvent in the extraction and purification of some antibiotics, alkaloids, vitamins, and flavors; as a solvent for lacquers, floor polishes, artificial silk manufacture, resins, fats, greases, gums, waxes, adhesives, oils, and rubber; as an industrial solvent in photography and dry cleaning; as a heat transfer medium in fire extinguishers; and as an intermediate in the preparation of dyes and pesticides. Chloroform is also a common dehalogenation product of carbon tetrachloride in anaerobic aquifers.

Chloroform is a colorless, volatile, non-flammable liquid. It is slightly soluble in water and is miscible with oils, ethanol, ether, and other organic solvents. Chloroform has a pleasant, nonirritating odor. It is unstable when exposed to air, light, and/or heat, which cause it to break down to phosgene, hydrochloric acid, and chlorine. When heated to decomposition, chloroform emits toxic fumes of hydrochloric acid and other chlorinated compounds.

Chloroform has been detected in the atmosphere at concentrations ranging from about 0.02 to about 13 $\mu g/m^3$ and in indoor air at about 0.07 to about 3.6 $\mu g/m^3$. Foods such as seafood, dairy products, meat, oils/fats, vegetables, bread, and beverages may contain small amounts of chloroform, and drinking water supplies often contains chloroform as a by-product of chlorination. Chloroform is used in a number of industries, including building and paperboard industries, iron and steel manufacturing, internal combustion engine industries, pesticide manufacturing, breweries, dry cleaning, and food processing industries.

Chloroform is a recognized pollutant of both air and water. It is regulated in the United States by the EPA under the Clean Water Act (CWA), the Comprehensive Environmental Response, Compensation, and Liability Act (CERCLA), the Federal Insecticide, Fungicide, and Rodenticide Act (FIFRA), the Food, Drug, and Cosmetic Act (FD&CA), the Resources Conservation and Recovery Act (RCRA), the Safe Drinking Water Act (SDWA), and the Superfund Amendments and Reauthorization ACT (SARA). The EPA has established water quality criteria for chloroform, effluent guidelines, rules for regulating hazardous spills, gene threshold amounts, and requirements for handling and disposal of chloroform wastes.

Chloroform is regulated as a hazardous constituent of waste. A reportable quantity (RQ) of 10 lb. has been established for this material. EPA regulations require removal of chloroform from drinking water and establish a maximum contaminant level of 100 $\mu g/l$. The FDA also regulates chloroform as an indirect food additive for adhesive components in food packaging materials and as a component of materials that come into contact with food.

The use of chloroform in food, drugs, and cosmetics has been banned under the Food, Drug and Cosmetic Act. Prior to this ban, the FDA permitted the use of chloroform in cough preparations, liniments, cosmetics, and toothache drops. The National Institute of Occupational Safety and Health (NIOSH) recommends a 2-ppm short-term exposure limit of 60 minutes. And OSHA has established a permissible exposure limit of 2 ppm with no provision for a ceiling. Chloroform is subject to regulation by OSHA under the Hazardous Communication Standard and as a chemical hazard in laboratories.

Given this level of regulation and the common use of these compounds in industrial processes, methods must be found to remediate contaminated sites as completely as possible in an efficient manner. The present invention provides an effective and highly efficient biological treatment of halocarbons to remediate contaminated sites to levels which meet or exceed government regulations.

REPORTED DEVELOPMENTS

Several bacterial strains are known to produce enzymes which can degrade aerobically the chlorinated solvent trichloroethylene (TCE), an unsaturated aliphatic halocarbon. (Ensley, B. 1991. *Ann. Rev. Microbiol.* 45:283–299; Little, C. D., et al., 1988. *Appl. Environ. Microbiol.* 51:951–956; Nelson, M. J. K. et al., 1988. *Appl. Environ. Microbiol.* 54:604–606; Shields, M. S., et al., 1989. *Appl. Environ. Microbiol.* 55: 1624–1629; Wackett, L. P., and D. T. Gibson. 1988. *Appl. Environ. Microbiol.* 54:1703–1708.) In recent evaluations of TCE and chloroform degradation by enrichment cultures comprising a consortia of bacteria strains capable of degrading toluene and phenol, Chang and Alvarez-Cohen concluded that strains that produce enzymes called "aromatic oxygenases" are capable of degrading unsaturated hydrocarbons, such as toluene, TCE, and benzene, but are not able to degrade saturated hydrocarbons (CF, 1,2-DCA, methane, hexane, etc.). (Chang, H-. L., and L. Alvarez-Cohen. 1995. *Environ. Sci. Technol.* 29:2357–2367; Chang, H-. L., and L. Alvarez-Cohen. 1995, *Biotechnol. Bioeng.* 45:440–449.)

Aromatic oxygenases are frequently involved in the degradation of hydrocarbons. One such aromatic oxygenase is toluene-4-monooxygenase (T4MO) which is involved in TCE degradation by the bacterial strain *Pseudomonas mendocina* KR1.

The role of toluene-4-monooxygenase in TCE degradation by *P. mendocina* KR1 was confirmed by cloning the T4MO genes into *E. coli* and showing that the recombinant strain was capable of degrading TCE. (Winter, R., et al., 1989. *Bio/Technology.* 7:282–285; Winter et al., U.S. Pat. No. 5,079,166.) A study by Jahng and Wood demonstrated that chloroform was not degraded by *P. mendocina* KR1 or several other aromatic oxygenase-producing bacteria even though these bacteria were able to degrade trichloroethylene. (Jahng, D. and T. K. Wood. 1994. *Appl. Environ. Microbiol.* 60: 2473–2482).

Various studies have evaluated the aerobic biodegradation of chloroform by methanotrophic bacteria. (Alvarez-Cohen, L, et al., 1992. *Appl. Environ. Microbiol.* 58:1886–1893; Alvarez-Cohen, L. and P. L. McCarty. 1991. *Appl. Environ. Microbiol.* 57:228–235; Chang, H-. L., and L. Alvarez- Cohen. 1995. *Environ. Sci. Technol.* 29:2357–2367; Henson, J. M., M. V. Yates, and J. Cochran. 1989. *J. Ind. Microbiol.* 4:29–35; Strand, S. E., and L. Shippert. 1986. *Appl. Environ. Microbiol.* 52:203–205; Tsien, H. -C., et al., 1989. *Appl. Environ. Microbiol.* 55:3155–3161.) Pure cultures of the methanotrophic bacteria *M. trichosporium* OB3b are capable of degrading many chlorinated aliphatic hydrocarbons. The role of the enzyme-soluble methane monooxygenase (sMMO) produced by these bacteria in chlorinated solvent degradation has been demonstrated. (Oldenhuis, R., et al., 1989. *Appl. Environ. Microbiol.* 55:2819–2816; Tsien, H. -C., et al., 1989. *Appl. Environ. Microbiol.* 55:3155–3161; Fox B. G., et al. 1990. *Biochemistry.* 29:6419–6427.)

Although methanotrophic bacteria have been used for remediating TCE-contaminated environments via horizontal wells at the Savannah River Site Integrated Demonstration Project, their utility is limited by stringent growth requirements. only methane or methanol can serve as growth substrates; and, under optimal growth conditions, their growth rate is significantly slower than the growth rate of toluene-degrading Pseudomonads. (Brockman, F. J., et al., 1995. *J. Haz. Material.* 41:287–298.; Hazen, T. C. et al., 1994, *In situ Remediation: Scientific Basis for Current and Future Technologies*, Battelle Press, Richmond, Wash.; pp. 137–150; Lombard et al., 1994, R. E. Hinchee (ed.) *Air Sparging for Site Remediation*, Lewis Publishers, Boca Raton, Fla., pp. 81–96; Semprini, L., and P. L. McCarty. 1991. *Ground Water* 29:365–374; Jahng, D. and T. K. Wood. 1994. *Appl. Environ. Microbiol.* 60:2473–2482.) Furthermore, expression of sMMO in some well characterized strains is inhibited by low concentrations of copper (>4.5 $\mu$M) in the growth medium. Also, methane can act as a competitive inhibitor of chlorinated solvent oxidation. (Tsien, H. -C., et al., 1989. *Appl. Environ. Microbiol.* 55:3155–3161.; Prior, S. D. and H. Dalton. 1985. *J. Gen. Microbiol.* 131:155–163; Oldenhuis, R., et al., 1989. *Appl. Environ. Microbiol.* 55:2819–2816; Speitel, G. E., et al., 1993. *Water Res.* 27:15–24.)

Another potential limitation on the use of methanotrophics is their low ratio of contaminant converted to growth substrate utilized. Landa and colleagues reported a conversion ratio of 0.008–0.4 $\mu$mol TCE/mmol methane for *M. trichosporium* OB3b, whereas *B. cepacia* G4 had a conversion ratio of 10–50 $\mu$mol TCE/mmol toluene oxidized. (Landa, A. S. et al., 1994. *Appl. Environ. Microbiol.* 60:3368–3374.) It was observed also that *M. trichosporium* OB3b was more susceptible to inactivation through TCE degradation than *B. cepacia* G4, possibly because the intermediates generated by sMMO are more harmful, or because *B. cepacia* G4 is less susceptible to damage by the intermediates on an organismal level.

In addition to the above-cited problems of stringent growth requirements and copper inhibition, the growth of methanotrophic organisms on methane can require the use of explosion-proof equipment, which adds significantly to the cost of setting up a remediation facility. Accordingly, use of the methanotrophic organisms is inefficient due to growth rates of the microorganisms and is potentially dangerous. Accordingly, methanotrophics are not viable alternatives to conventional disposal methods.

To circumvent some of the limitations of working with methanotrophics, the sMMO genes from these microorganisms were cloned into several aromatic oxygenase-producing bacteria including *P. mendocina* KR1, *P. putida* F1, and *B. cepacia* G4. Only *P. putida* F1 containing cloned methane monooxygenase genes degraded chloroform, but the rate of TCE and chloroform oxidation by the recombinant strain was at least 8 times lower than that of the natural methane oxidizer, *M. trichosporium* OB3b. Furthermore, the phenotype was unstable, with only 10 to 20% of the cultures inoculated able to efficiently degrade organo-halides. Chloroform was not degraded by the toluene oxidizing strains *P. putida* F1 and *B. cepacia* G4 without the cloned genes, or by *P. mendocina* KR1 with or without cloned methane monooxygenase genes.

Chloroform degradation has been demonstrated also in anaerobic enrichment cultures and in pure cultures of a methanogenic bacterium. (Bouwer, E. J., and P. L. McCarty. 1983. *Appl. Environ. Microbiol.* 45:1286–1294; Bouwer, E. et al., 1981. *Environ. Sci. Technol.* 15:596–599; Van Beelen, P., and F. Van Keulen. 1990. *Hydrobiol. Bull.* 24:13–22; Bagley, D. M., and J. M. Gossett. 1995. *Appl. Environ. Microbiol.* 61:3195–3201.; Mikesell, M. D., and S. A. Boyd. 1990. *Appl. Environ. Microbiol.* 56:1198–1201.) Egil and colleagues observed, however, that anaerobic dehalogenation of chloroform by several methanogenic organisms was not enzymatically mediated, and that the reaction could be catalyzed even by autoclaved cells. (Egli, C., et al., 1987. *FEMS Microbiol. Lett.* 43:1295–1299.)

SUMMARY OF THE INVENTION

In accordance with the present invention, there is provided a method for degrading a saturated aliphatic halocarbon by contacting said saturated aliphatic halocarbon with aromatic oxygenase-producing bacteria.

Examples of preferred species of aromatic oxygenase-producing bacteria are *Pseudomonas mendocina* KR1, ATCC 55706, Strain ENVPC5; and Strain ENVBF1 ATCC 55819.

Also, in accordance with an embodiment of the present invention, a co-substrate is utilized to increase the cell population of the microorganism. For this purpose, the microorganism is grown on co-substrates such as, for example, phenol, alkanes, and typical bacterial growth substrates, for example, Lauria or nutrient broth.

Another aspect of the present invention includes degrading the saturated aliphatic halocarbon by contacting it with a recombinant microorganism comprising a host microorganism containing a cloned aromatic oxygenase gene.

An additional aspect of the present invention includes degrading the saturated aliphatic halocarbon by contacting it with the microorganism in a bioreactor, for example, a suspended growth bioreactor, a fixed film bioreactor such as a fluid bed reactor or a biotrickling filter, or a biofilter reactor.

Still another aspect of the present invention includes degrading the saturated aliphatic halocarbon with the microorganism in situ.

In another aspect, the present invention provides bacteria for degrading saturated aliphatic halocarbons, in particular Pseudomonas sp. ENVBF1.

In yet another embodiment, the present invention provides recombinant microorganisms for degrading saturated aliphatic halocarbons, such recombinant microorganism comprising a host microorganism containing a cloned aromatic oxygenase gene.

The present invention provides means for degrading a saturated aliphatic halocarbon, for example, chloroform, bromoform, and 1,2-dichloroethane, efficiently and economically. It can be used to completely degrade these compounds to innocuous compounds such as $CO_2$, water, and chloride or bromide salts. In contrast, prior art techniques require the use of adsorbents such as activated carbon, and large expenditures of energy to burn the contaminant; or they require that the adsorbed halocarbons be placed in landfills where they may once again become environmental hazards.

In contrast, the present invention provides biological methods for degrading saturated aliphatic halocarbons utilizing easily grown microorganisms which can efficiently and economically degrade a variety of saturated aliphatic halocarbons utilizing readily available equipment regardless of whether the degradation is to be performed off-site or at the site of contamination. Other advantages of the present invention will become apparent from a consideration of the following detailed description of the invention.

DETAILED DESCRIPTION OF THE INVENTION

Figure 1:
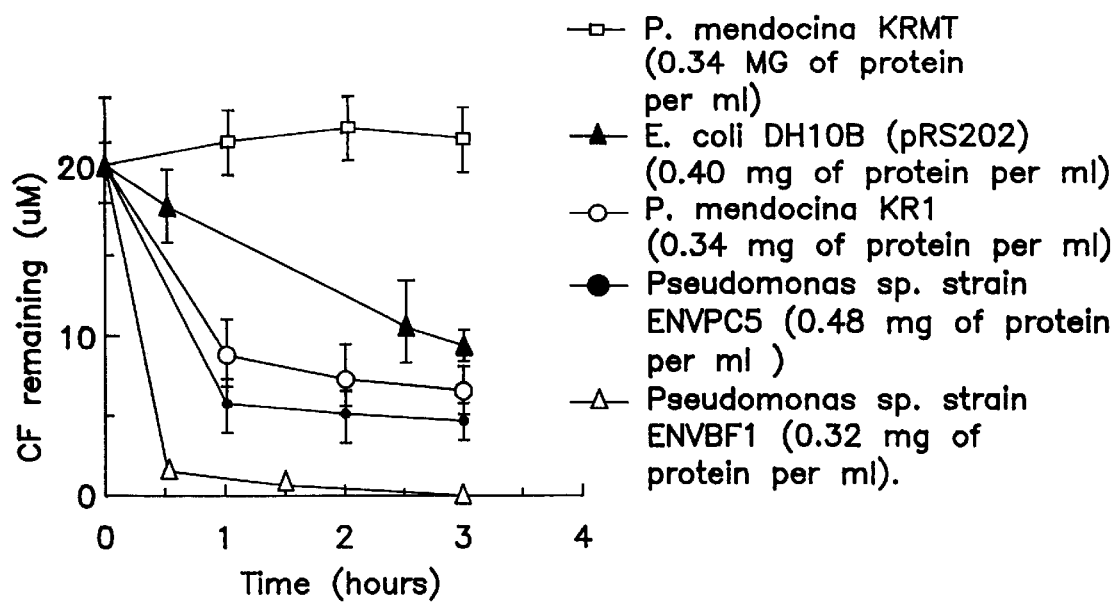
FIG. 1 is a graph which shows degradation of CF by *P. mendocina* KR1, *P. mendocina* KRMT, Pseudomonas sp. Strain ENVPC5, Pseudomonas sp. Strain ENVBF1, and *E. coli* DH10B (pRS202).

There follows a description of compounds that can be degraded by practice of the present invention, the microorganisms which may be used to degrade the compounds and methods for promoting degradation, including treatment in situ and treatment in a bioreactor.

Compounds that can be Degraded

The present invention can be used to degrade saturated aliphatic halocarbons, including chloro-, bromo-, iodo-, and fluoro-containing compounds, for example, alkanes having the general formula $C_nH_{2n+2}$ wherein at least one hydrogen atom has been replaced by a halogen selected from chlorine, bromine, iodine and fluorine. The compounds may contain two or more different halogen atoms and may contain one or more hydrogen or other non-halo elements. Preferably, the halocarbon that is degraded in accordance with the invention has from 1 to about 10 carbon atoms, more preferably from 1 to about 5 carbon atoms, and contains one or more halogens selected from chlorine and bromine. Examples of common saturated aliphatic halocarbons which may be degraded include chloroform ($CHF_3$), bromoform ($CHBr_3$), 1,2-dichloroethane [(1,2 DCA) ($H_2ClC-CClH_2$)], 1,2 dibromoethane, monochloroethane, and monobromoethane. Excellent results have been achieved in degrading halocarbons that have 1 or 2 carbon atoms.

It is believed that the present invention will be used most widely in the degradation of chloroform and other prevalent chlorine-containing environmental contaminants. Nevertheless, the present invention can be used also to remediate a variety of other saturated aliphatic halocarbons which may not necessarily be considered as environmental contaminants. A mixture of different saturated aliphatic halocarbons also can be degraded by using one or a mixture of the microorganisms disclosed.

For any given saturated aliphatic halocarbon it is possible to determine if a given microorganism containing an aromatic oxygenase degrades the halocarbon using conventional laboratory assays, such as gas chromatography. A specific example of an assay which may be used to determine if a given halocarbon can be degraded using the methods of the present invention is provided hereinbelow in Examples 1 and 2.

The extent of degradation of a given saturated aliphatic halocarbon will vary according to the type of saturated aliphatic halocarbon and the type of aromatic oxygenase present in the microorganism. The extent of degradation will be influenced also by physical parameters during the remediation treatment including time, temperature and pH conditions. In general, the federal or state guidelines regarding acceptable levels of a given compound may serve as guidelines for the extent of remediation at a given site. It is preferred in the practice of the present invention that the halocarbon be fully degraded or "mineralized". The term "mineralized" refers to a reaction(s) in which the halocarbon is degraded to carbon dioxide, water and a salt of the halogen. To determine the extent of mineralization, various assays can be performed. Two particularly useful assays which can be performed to determine the extent of mineralization are presented in Example 3 and Example 4 below.

Microorganisms

In general, bacteria possessing an aromatic oxygenase capable of degrading a saturated aliphatic halocarbon can be used in the practice of the invention. "Oxygenase", as the term is used herein, refers to bacterial enzymes which catalyze the incorporation of one or both atoms of a molecule of oxygen into a molecule of substrate. The term "aromatic oxygenases" refers to an enzyme that can oxidize a compound possessing an aromatic ring, such as, for example, toluene, benzene and xylene or other aromatic ring-containing compounds, including compounds containing more than one aromatic ring. The term "monooxygenase" refers to an enzyme which catalyses the incorporation of one atom of oxygen into a molecule of substrate, the other oxygen being reduced to water. An example of such an aromatic oxygenase is toluene-4-monooxygenase (T4MO) which is involved in TCE degradation by the bacterial strain *Pseudomonas mendocina* KR1.

Although a variety of aromatic oxygenase enzymes are useful in the practice of the present invention, bacteria which produce or which are modified genetically to produce the aromatic oxygenase toluene monooxygenase are particularly preferred in the practice of the present invention.

Examples of microorganisms which contain aromatic oxygenases and which can be used in the present invention include *Pseudomonas mendocina* KR1, ATCC 55706; Pseudomonas sp. Strain ENVPC5; and Pseudomonas sp. Strain ENVBF1, ATCC 55810.

The preferred microorganism for use in in situ and bioreactor-based remediation is Pseudomonas sp. Strain ENVBF1.

Envirogen Pseudomonas sp. strain ENVBF1 was deposited in the American Type Culture Collection on Sep. 4, 1996, and was assigned ATCC number 55819.

Microorganisms for use in the practice of the present invention, for example, the strains identified above, can be isolated from hydrocarbon contaminated soil by enrichment culturing, using techniques commonly used by those skilled in the art and previously described in the literature. (McClay, K., et al., 1995. *Appl. Environ. Microbiol.* 61:3479–3481.) Procedures which can be used to identify and isolate other strains that can be used in the practice of the invention are presented in Example 5 and Example 6.

The present invention includes within its scope the use of mutagenesis to improve the ability of the microorganisms to degrade a given compound or to survive in a given medium contaminated with the compound. Standard bacterial mutagenesis techniques known in the art can be employed to mutagenesis the bacteria. Alternatively, the bacteria can be modified using genetic engineering to add or delete given genes that effect the bacteria's ability to degrade a given compound.

The present invention includes also within its scope the use of one or more other microorganisms in combination with one or more of the microorganisms described herein to achieve complementary degradation against a mixture of contaminants which includes a saturated aliphatic halocarbon, for example, in the treatment of mixed waste streams. Such a combination utilizes the different degradative specificities of the involved microorganisms. Accordingly, for certain applications, a given contaminated medium can be treated with microorganisms having different specificities for given contaminants or their degradative intermediates.

For some applications, it may be desirable to introduce genes encoding an aromatic oxygenase into a microorganism that is especially suited to a given environment or which has certain growth requirements. Accordingly, bacteria which have been transformed with a plasmid or other vector containing the gene or genes for an aromatic oxygenase may be used in the practice of the present invention. A procedure for transforming bacteria with an aromatic oxygenase gene is presented hereinbelow in Example 7. This procedure may be modified as necessary to introduce any cloned aromatic oxygenase into a given bacterial species.

In Situ and Ex Situ Biodegradation

Depending on a variety of factors, it may be desirable to remove contaminated material from a given site and treat the material off-site in a bioreactor. Alternatively, it may be desirable to treat the site in situ. A determination of which treatment method is preferable depends on a variety of factors, including the site of the contamination, the extent of contamination, the type of contaminant and the relative costs of using either method.

In general, the degradation can take place under a wide range of conditions. Exemplary conditions include a temperature in the range of between about 4 to about 42° C., preferably from about 25 to about 35° C., and at a pH from about 6 to about 8, preferably from about 6.8 to about 7.2.

Growth of the bacteria can be effected in a bioreactor or in situ and can be enhanced by the addition of growth substrates which are more readily metabolized by the microorganisms.

Conventional bacterial growth media can also be used to effect an increase in cell population. Examples of such growth media are: Lauria broth (Gibco/BRL); Trypticase soy agar (BBL; Bectin/Dickinson, Cockysville, Md.); R2A (Difco Laboratories, Detroit, Mich.); and nutrient broths, including casamino acids and/or yeast extract.

Once the cell population has reached a desirable level, it may be desirable to introduce a co-substrate which promotes expression of the genes responsible for degradation of the saturated aliphatic halocarbon. Preferably a co-substrate is provided during the treatment, for example, in a concentration similar to that of the saturated aliphatic halocarbon. The co-substrate preferably is an aromatic compound, more preferably an aromatic compound selected from the group consisting of toluene, phenol, benzene, ethylbenzene, and xylene.

The saturated halocarbons may be treated in aqueous media, in soil or in a vapor phase, e.g. air, by contact with a microorganism that produces an aromatic oxygenase. The preferred procedures to be used in treatment of a contaminated site are presented in more detail hereinbelow.

Degradation of Saturated Halocarbons by Aromatic Oxygenase-Producing Bacteria in Bioreactors In accordance with the present invention, the aromatic oxygenase-producing bacteria can be used to degrade the saturated aliphatic halocarbons in a bioreactor. The procedure used can be similar to that disclosed in B. D. Ensley and P. R. Kurisko, 1994. *Appl. Environ. Microbiol.* 60:285–290.

In one such treatment approach, saturated aliphatic halocarbons in water are degraded by passing the contaminated water through a fluid-bed reactor that has been inoculated with aromatic oxygenase-producing bacteria such as *P. mendocina* KR1, strain ENVPC5, or strain ENVBF1. The fluid bed reactor is, for example, a stainless steel cylinder (reactor vessel) connected to an equilibration tank, a nutrient feed tank for delivery of nutrients (e.g. soluble fertilizer) and co-substrates (e.g. toluene, phenol, benzene xylene or ethylbenzene), a pH control system consisting of tanks for caustic and acid feed controlled by chemical delivery pumps, a pH controller, and a pH probe, an oxygen delivery system consisting of a bubbleless oxygen diffuser, bottled oxygen, and an oxygen meter and probe, and an effluent collection tank. The reactor vessel is filled with granular activated carbon or sand ("reactor bed") which acts as a growth support for microbial biomass.

The reactor is operated by collecting saturated aliphatic halocarbon-contaminated water in the equilibration tank, then pumping it into the bottom of the reactor vessel at a flow rate that results in the fluidization of the granular activated carbon or sand in the reactor vessel. In one example, the reactor is operated at an influent flow rate that results in a 20% increase in the reactor bed volume. As the influent stream passes from the equilibration tank to the reactor vessel, nutrients are added to create a C:N:P ratio of approximately 100:10:1 by adding soluble fertilizer (e.g. Lesco 19,19,19) to the influent stream with a chemical metering pump. The pH of the influent stream is then adjusted by adding caustic solution or acid from the base or acid feed tanks so that the final pH of the influent is between, for example, pH 6.8 and pH 7.2. If the contaminant stream does not contain a co-substrate such as toluene, benzene, ethyl benzene, xylene or phenol, the co-substrates are added from a nutrient feed tank by using a chemical metering pump so that the final halocarbon:co-substrate ratio is between, for example, 6:1 and 10:1. As the halocarbon-contaminated water is passed up through the fluid bed reactor, the aromatic oxygenase-producing bacteria attached to the reactor bed material, as well as aromatic oxygenase-producing bacteria suspended in the liquid, degrade the halocarbon while using toluene or phenol as a co-substrate. Gasses released from the reactor are passed through a canister of granular activated carbon to trap any volatile contaminants that are not degraded in the reactor. Degradation of the halocarbon is measured by determining its concentration in the influent and effluent streams. For example, contaminant concentrations in the streams are determined by gas chromatography/mass spectroscopy using EPA Method 8260B. (US EPA.1986. Test methods for evaluating solid wastes. United States Env. Protection Agency. Pub. no. SW846.)

As an example, a reactor vessel with approximate dimensions of 1 ft diameter by 14 ft. high with an empty bed volume of 66 gal., would utilize approximately 210 lbs. of granular activated carbon or sand and the reactor would be operated at an influent flow rate of up-to 10 gal/min. (gpm).

In Situ Degradation of Saturated Halocarbons by Aromatic Oxygenase-Producing Bacteria Saturated aliphatic hydrocarbons can also be biodegraded by aromatic oxygenase-producing bacteria in contaminated media without removing the contaminated media. This process is referred to as "in situ biological treatment". The process can be facilitated by adding aromatic oxygenase-producing bacteria to the contaminated media, a process known as "bioaugmentation", or by enhancing the activity of naturally-occurring aromatic oxygenase-producing bacteria, a process known as "biostimulation".

In one exemplary embodiment of the present invention, aromatic oxygenase-producing bacteria are added directly to saturated halocarbon-contaminated aquifers. The method involves growing large amounts of aromatic oxygenase-producing bacteria such as, for example, *P. mendocina* KR1, ENVPC5, or ENVBF1, in a fermentor, such as those available from Abec, Inc. Allentown, Pa., using standard fermentation procedures known to those skilled in the art. (Antonio Trilli. 1986. Scale-up fermentations. pp. 277–307 in Arnold L. Demain and Nadine A. Soloman (eds.) "Manual of Industrial Microbiology and Biotechnology." American Society for Microbiology, Washington, D.C.) The bacteria (e.g. *P. mendocina* KR1, ENVPC5 or ENVBF1) are grown in BSM medium with phenol as a growth substrate and an inducer of the aromatic monooxygenase genes. The cells are grown to an optical density at 550 nm of between 20 and 40 (approximately 2 to $4 \times 10^{10}$ cells/ml) and collected in a tank for transport to a contaminated site. Alternately, the organisms are grown on-site by using a field fermentor and the same growth conditions.

The bacteria are injected into the contaminated aquifer through wells inserted into the contaminated zone of the media. Alternately, they are injected into a stream of groundwater that is recovered from one area of the aquifer and re-injected into the contaminant plume. Oxygen is supplied to the organisms by air sparging, which requires injecting air or oxygen into wells that are inserted into or below the contaminated media. (Marley, M. C., D. J. Hazebrook, and M. T. Walsh. 1992. *Groundwater Monitoring Review* 2:137–145.) Alternately, oxygen is provided to the aromatic oxygenase-producing bacteria by adding hydrogen peroxide or slow release oxygen products (eg. $MgO_4$) to the contaminated media, or by passing recirculated groundwater through a down-flow bubble contactor and injecting oxygenated water into the contaminated media. Additional aromatic oxygenase-producing bacteria are added as needed to completely degrade the saturated halocarbon contaminants.

Contaminant degradation in situ is measured by collecting groundwater and/or soil samples from recovery wells within, and around, the contaminant plume both before and after injection of the aromatic oxygenase-producing bacteria. The samples are analyzed by gas chromatography/mass spectroscopy as described previously to measure changes in the concentration of saturated halocarbons.

EXAMPLES

Presented hereinbelow are examples which are illustrative of the present invention.

Example 1

This example illustrates the use of the present invention and also contains a description of an assay which can be used to determine if a given organism degrades chloroform. The assay can be used to determine the ability of a given microorganism to degrade other halocarbons by substituting the other halocarbon for chloroform in the procedure presented below.

The strains to be tested were grown at 30° C. in BSM with toluene in the vapor phase. The cultures were harvested at an $OD_{550}$ between 0.6 and 1.0. The cells were collected by centrifugation, washed with BSM, and suspended in fresh BSM to an $OD_{550}$ of 2.

*E. coli* DH10B (pRS202) containing the cloned tmo genes was grown to an $OD_{550}$ between 1 and 2 in LB media containing tetracycline (10 μg/ml) and IPTG (20 μg/ml).

Cells were then collected by centrifugation and suspended to an $OD_{550}$ of 2 in fresh LB with tetracycline and IPTG. The cell suspensions (5 ml) were added, in triplicate, to 15-ml serum vials and sealed with Teflon lined septa and aluminum crimp seals. Ten μl of 20 mM chloroform in methanol was injected through the septum of each sample to create a concentration of 20 μM assuming all the chloroform was in the aqueous phase. Control samples were prepared by adding chloroform to vials that contained BSM with no cells. The serum vials were then incubated on an orbital shaker (100 rpm) at 25° C. At predetermined time points, 10 μl samples of the headspace gas were removed with a Hamilton gas tight syringe (Reno, Nev.) and injected onto a Varian 3400 gas chromatograph (Walnut Creek, Calif.) equipped with a 30 m capillary Vocol column (Supelco Inc., Bellefonte, Pa.) and an electron capture detector. The column, injector, and detector temperatures were maintained at 160, 180, and 300° C., respectively. A 5-point calibration curve was prepared prior to each analysis by adding known amounts of chloroform to serum vials containing only water, and analyzing 10 μl of the headspace gas as described for the test samples. The detection limit for chloroform was <0.3 μM.

As initially demonstrated by headspace depletion assays, CF was degraded by *P. mendocina* KR1, Pseudomonas sp. Strains ENVPC5 and ENVBF1, and also by *E. coli* DH10B (pRS202) which contained cloned T4MO genes from *P. mendocina* KR1 (FIG. 1). In FIG. 1, the data points represent the mean ±SD of triplicate samples and the symbols have the following meanings: open square, *P. mendocina* KRMT (0.34 mg protein/ml); closed triangle, *E. coli* DH10B (pRS202) (0.40 mg protein/ml); open circle, *P. mendocina* KR1 (0.34 mg protein/ml); closed circle, Pseudomonas sp. Strain ENVPC5 (0.48 mg protein/ml); open triangle, Pseudomonas sp. Strain ENVBF1 (0.32 mg protein/ml). Chloroform was not degraded by the tmo mutant *P. mendocina* KRMT, *B. cepacia* G4, *P. putida* F1, *P. picketti* PKO1, or Pseudomonas sp. Strain ENV113 (data not shown). Of the strains tested, the rate of CF degradation was greatest in Pseudomonas sp. Strain ENVBF1. In each culture, the initial degradation of CF was rapid, but decreased upon extended incubation (FIG. 1). For example, strain ENVBF1 degraded 1.9 nmol CF/min/mg cell protein during the first half hour of incubation. However, during the following hour of incubation, the CF degradation rate decreased to 0.05 nmol CF/min/mg cell protein. Strain ENVPC5 and *P. mendocina* KR1 had initial CF degradation rates of 0.48 and 0.49 nmol CF/min/mg cell protein in the first hour of incubation, respectively, which decreased to 0.024 and 0.078 nmol CF/min/mg cell protein, respectively, during the second hour of incubation.

Example 2

This example is illustrative of an assay for determining if a given microorganism or recombinant microorganism can degrade halocarbons other than chloroform and also illustrates practice of the present invention. To compare the substrate range of the various aromatic oxygenase enzymes evaluated in this study, toluene-induced cells were incubated for 3 hr with 20 μM of either 1,2-DCA, TCE, CF, or a mixture of cis- and trans-DBE. Experiments and analysis were performed by using the gas chromatography method, essentially as described above. Table 1 shows the results of halocarbon degradation by a variety of aromatic oxygenase-producing strains.

TABLE 1

Degradation of halogenated organic compounds by toluene-oxidizing strains

| Organism[1] | 1,2-DCA | TCE | CF | cis-DBE[2] | trans-DBE[1] |
|---|---|---|---|---|---|
| P. mendocina KR1 | 2.7(0.1) | 0 | 4.7(0.15) | 9.1(0.4) | 0.9(0.2) |
| P. putida F1 | 19(0.3) | 0 | 20(1.3) | 0.45(0.1) | 0.75(0.5) |
| B. cepacia G4 | 20(1.9) | 0 | 20(0) | 0.2(0.03) | 2.6(0.5) |
| P. picketti PKO1 | 20(0.3) | 0 | 20(0.1) | 2.7(0.7) | 1.9(0.09) |
| Strain ENV113 | 18[3] | 0 | 20(0) | 0.37(0.2) | 2.7(0.1) |
| Strain ENVBF1 | 18(0.5) | 0 | 1.6(0.1) | 0.39(0.1) | 2.4(0.5) |
| Strain ENVPC5 | 2.8(0.7) | 0 | 4.6(0.2) | 8.8(0.9) | 1(0) |

All samples were incubated 3 hr. at 25° C. Data represents the mean (SD) of triplicate samples.
[1]Total cell protein concentrations (mg protein/ml) of the 5-ml cultures tested were: KR1, 0.33; F1, 0.56; G4, 0.33; PKO1, 0.54; ENV113, 0.33; ENVBF1, 0.32; and ENVPC5, 0.48.
[2]cis- and trans-DBE were added as a 50/50 mixture to a combined concentration of 20 μM; all other compounds were added as separate components to a final concentration of 20 μM based on the amount of liquid in the sample.
[3]Result from a single sample.

The T4MO mutant P. mendocina KRMT did not degrade any of the compounds tested, even when toluene was supplied as an inducer in the sample headspace. Each of the strains that degraded CF also completely degraded BF.

Figure 2:
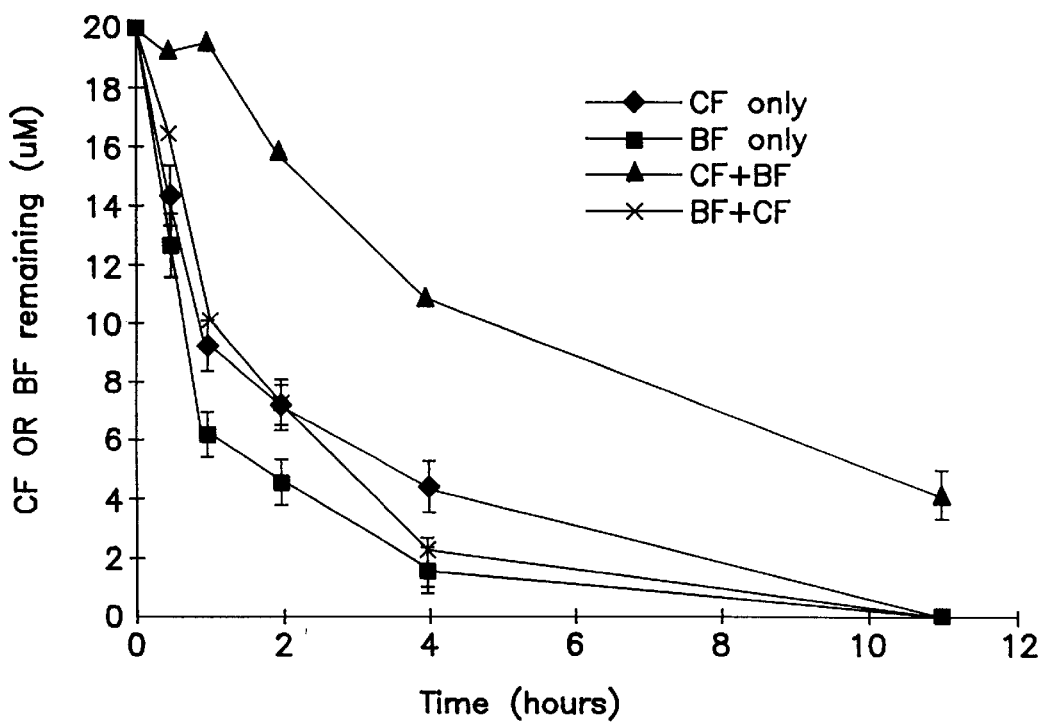
FIG. 2 is a graph which shows degradation of bromoform ("BF") and chloroform ("CF") by the recombinant aromatic oxygenase-producing organism, *E. coli* DH5α (pRS202).

FIG. 2 shows bromoform degradation by P. mendocina KR1 in the presence and absence of chloroform. Cultures were incubated with 20 μM BF, 20 μM CF, or 20 μM of both BF and CF. The data points are the mean ± standard deviation of triplicate samples. Symbols: diamond, CF only; square, BF only; triangle, CF degradation in the presence of BF; "x", BF degradation in the presence of CF. As shown in FIG. 2, while the presence of BF inhibits CF degradation, the presence of CF does not inhibit BF degradation.

The results demonstrate that bromoform is degraded preferentially over chloroform by this strain, but also that a mixture of saturated halocarbons can be degraded to innocuous products by bacteria that produce aromatic oxygenases.

The results of this study also suggest that the type of aromatic oxygenase enzyme utilized by a microorganism affects the range of halocarbons that it can oxidize. P. mendocina KR1 is known to express a toluene p-monooxygenase, and the results of this study suggest that a similar enzyme is produced by strain ENVPC5 (Table 1). (Whited, G. M., and D. T. Gibson. 1991. J. Bacteriol. 173:3017–3020.) Both strains were capable of oxidizing CF and other saturated hydrocarbons. Chloroform was not oxidized by the toluene dioxygenase-producing strain P. putida F1, or by two toluene o-monooxygenase-producing strains, ENV113 and B. cepacia G4. P. picketti PKO1 which produces a toluene-3-monooxygenase did not oxidize CF or 1,2-DCA (Table 1). (Olsen, R. H.,et al., 1994. J. Bacteriol. 176: 3749–3756.) Strain ENVBF1, which also appears to produce a toluene o-monooxygenase (Table 1), but is capable of growth on all three cresol isomers, degraded CF at the greatest rate of the strains tested. These results suggest that the apparent T2MO produced by this strain is biochemically different from those produced by strains G4 and ENV113.

A similar pattern of substrate specificity was observed during degradation of cis- and trans-DBE (Table 1). Each of the T4MO-producing strains degraded trans-DBE at a greater rate than cis-DBE, whereas the T2MO producing strains preferentially degraded cis-DBE.

Example 3

This example illustrates the use of the present invention to degrade chloroform, a saturated aliphatic halocarbon and is also is illustrative of an assay that can be performed in order to verify that chloroform is being fully mineralized in the bottle assays of Example 1 (Jahng, D. and T. K. Wood. 1994. Appl. Environ. Microbiol. 60: 2473–2482).

P. mendocina KR1 was grown on toluene, harvested, washed, and suspended in 0.1 M potassium phosphate buffer, pH 7.0, to an $OD_{550}$ of 2. Five ml samples of the culture were then sealed in 15 ml serum vials, and 0.3 μmoles of chloroform in 15 μl of methanol was added to each vial to give a final chloroform concentration of 60 μM. The two controls used in this experiment consisted of wild-type P. mendocina KR1 without the addition of chloroform, and P. mendocina KRMT grown on glutamate with toluene in the headspace. An additional 0.1 μl of toluene was injected into each of the experimental vials, by using a 1.0 μl syringe, to enhance the long term degradation of chloroform. The vials were then shaken at 100 rpm at 25° C. for 20 hours (a period of time found sufficient to allow completion of chloroform degradative activity), and the amount of chloroform degraded was determined by gas chromatography as described above. The vials were then opened and allowed to passively ventilate for 12 hours—to allow evaporation of unreacted chloroform. This was necessary because residual chloroform interferes with the chloride ion analysis. The samples were then centrifuged to remove the cells, and the supernatant fractions were analyzed for chloride on a DX-100 ion chromatograph (Dionex, Marlton, N.J.), equipped with a 4 mm AS4A8C column, and a conductivity detector calibrated for chloride. The eluant was 1.8 mM sodium carbonate, and 1.7 mM sodium bicarbonate, with a flow of 2 ml per minute. All samples were analyzed in triplicate.

The results of chloride ion analysis are presented in Table 2.

TABLE 2

Release of Chloride Ions from the Degradation of Chloroform by P. mendocina KR1

| Organism | CF initial (μM) | CF degraded (μM) | Theoretical chloride ion yield (μM) | Chloride ion detected (μM) | Yield % |
|---|---|---|---|---|---|
| P. mendocina KR1[1] induced | 60 | 38.4 | 115 | 135(2.8) | 74[4] |
| P. mendocina KR1[2] control | 0.0 | 0.0 | 0.0 | 48.9(8.6) | NA |
| P. mendocina KRMT[3] | 60 | 0.0 | 0.0 | 51.6(5.6) | NA |

All samples were incubated for 20 hours at 25° C. Data represents the mean (standard deviation) of triplicate analysis.
[1]Grown with toluene as sole carbon source.
[2]TMO mutant of P. mendocina KR1 grown on glutamate, with toluene in the vapor phase.
[3]Grown with glutamate as sole carbon source.

TABLE 2-continued

Release of Chloride Ions from the
Degradation of Chloroform by *P. mendocina* KR1

| Organism | CF initial ($\mu$M) | CF degraded ($\mu$M) | Theoretical chloride ion yield ($\mu$M) | Chloride ion detected ($\mu$M) | Yield % |
|---|---|---|---|---|---|

[4]Value corrected for amount of chloride found in controls (i.e., 135 $\mu$M − 85, 85/115 = 74%)
NA-Non-applicable.

Gas chromatographic analysis demonstrated that *P. mendocina* KR1 (1.7 mg cell protein in 5 ml) degraded 38.4 $\mu$M of CF during an overnight incubation in the presence of 60 $\mu$M of CF. The theoretical yield of chloride ions from the destruction of 38.4 $\mu$M of CF is 115 $\mu$M Cl−. The triplicate samples from the two control treatments containing either toluene induced cells without CF or the tmo mutant, *P. mendocina* KRMT (containing an inactive tmo gene), contained 48.9±8.6 $\mu$M (SD for n=3) and 51.6±5.6 $\mu$M of chloride ions after incubation, respectively. Cultures of toluene induced *P. mendocina* KR1 that degraded CF contained 135±2.8 $\mu$M chloride. After correcting for the background chloride present in the toluene-grown cells without CF, 74% of the theoretical yield of chloride ions (86.1 $\mu$M Cl−) was obtained from the biological destruction of CF by *P. mendocina* KR1. These results clearly demonstrate that aromatic oxygenase-producing bacteria can convert saturated halocarbons to innocuous products.

Example 4

This example is illustrative of an assay which may be used in order to confirm that chloroform is mineralized to $CO_2$ by a given microorganism.

*P. mendocina* KR1, Pseudomonas sp. strain ENVPC5, and Pseudomonas sp. strain ENVBF1, toluene-grown cells were incubated with [$^{14}$C] chloroform. Fractionation of the $^{14}$C-labeled products of chloroform degradation was performed by a modification of the method of Speitel and colleagues. (Speitel, G. E. et al., 1993. *Water Res.* 27:15–24.) Preliminary testing demonstrated that this method produced measurements of $^{14}CO_2$ production that were comparable to methods that rely on trapping $^{14}CO_2$ in an alkaline solution (data not presented). Toluene-grown cells were collected by centrifugation, rinsed with BSM, and suspended in BSM to an $OD_{550}$ of 1. Cell suspensions (7.5 ml) were then placed into 15-ml serum vials in quadruplicate, and 0.17 $\mu$Ci of [$^{14}$C] chloroform dissolved in 2 $\mu$l DMF (4.8 $\mu$M chloroform) was added. The vials were immediately sealed and incubated at 25° C. for 3 hr with shaking (100 rpm). To terminate the reactions and to draw gaseous $CO_2$ into the sample liquid, 75 $\mu$l of 2 N NaOH were injected through the septa. The vials were then returned to the shaker for 30 min.

After incubation, 100 $\mu$l of the culture liquid were removed through the septa, placed in 5 ml of OptiPhas 'Hi Safe III' scintillation cocktail (Wallac Scintillation Products, Turku, Finland), and the amount of radioactivity in each sample, as disintegrations per minute (dpm), was determined by liquid scintillation counting in a Wallac 1209 Rackbeta liquid scintillation counter (Pharmacia LKB Nuclear Inc., Gaithersburg, Md.). This basic fraction contained particulate (cell-bound) $^{14}$C, dissolved $^{14}CO_2$, and unreacted [$^{14}$C] chloroform, and was used as a measurement of "total" counts recovered. To liberate the dissolved $^{14}CO_2$ from the aqueous phase, 500 $\mu$l of 6 N HCl were added to each of the vials, and the acidified cultures were incubated for 30 min with shaking. A 100 $\mu$l aliquot of the culture was then withdrawn from each of the vials through the septa, and liquid scintillation counting was performed as described above. This acidic fraction contained soluble $^{14}$C-labeled compounds, but not $^{14}CO_2$. The difference in dpm between the basic fraction and the acidic fraction was a measure of the $^{14}CO_2$ formed from [$^{14}$C] chloroform.

To remove any additional volatile $^{14}$C-labeled compounds from the aqueous phase, the vials were opened and gently agitated overnight. The amount of radioactivity remaining in both the soluble and particulate form was measured by removing 100 $\mu$l of the overnight culture for scintillation counting. The remaining culture was then centrifuged to remove the particulate fraction, and 100 $\mu$l of the supernatant ("soluble" fraction) was removed for liquid scintillation counting. The "particulate" fraction was the difference in activity between the overnight culture and the "soluble" fraction. BSM without cells and uninduced (glutamate-grown) cells of Pseudomonas sp. Strain ENVBF1 served as controls. The total amount of $^{14}$C activity added was determined by adding 2 $\mu$l of the chloroform stock directly to 5 ml of scintillation cocktail and performing liquid scintillation counting.

Table 3 shows the results of [$^{14}$C]chloroform degradation by strains KR1, ENVBF1, and ENVPC5. Each test strain was incubated with 35 nmoles of [$^{14}$C]CF (3.7×10$^5$ dpm, 4.7 $\mu$M) in 7.5 ml of BSM. Because the Henry's law constant for CF at 25° C. is 0.15, and the headspace had the same volume as the liquid, the initial equilibrium CF concentration in the liquid was 3.9 $\mu$M, or 83% of the added CF. (Mackay D. and W. Y. Shiu. 1981. *J. Phys. Chem. Ref. Data* 10:1175–1199.)

TABLE 3

Biological oxidation of [$^{14}$C]chloroform
by toluene-grown *P. mendocina* KR1, Pseudomonas
sp. Strain ENVPC5 and Pseudomonas sp. Strain ENVBF1
Radioactivity from [$^{14}$C]chloroform[1]
Percent of Total Activity Added

| Strain | $CO_2$ | Soluble | Particulate | Total dpm |
|---|---|---|---|---|
| KR1 | 27(9.2) | 14(1.5) | 32(0.5) | 89(5.9) |
| ENVPC5 | 35(9.7) | 11(0.8) | 27(2.3) | 92(3.0) |
| ENVBF1 | 57(5.4) | 12(0.6) | 14(2.7) | 92(4.6) |
| Control | 0 | 0 | na | 92(5.9) |

[1]A total of 370 × 10$^3$ dpm (35 nmoles chloroform) was added to each 7.5 ml sample, and the samples were incubated for 3 h at 25° C. Protein concentrations for strains KR1, ENVPC5, and ENVBF1 were 0.17 mg/ml, 0.23 mg/ml, and 0.16 mg/ml, respectively. Values represent the percent of the total added activity measured in each fraction, and are the mean (SD) of triplicate samples.
[2]Cells grown under non-inducing conditions in BSM containing 0.4% sodium glutamate.
nd = not determined
na = not applicable Strain ENVBF1 converted the greatest amount of $^{14}$CF to $^{14}CO_2$, followed by strains ENVPC5 and KR1. Glutamate-grown ENVBF1 (control) did not convert $^{14}$CF to $^{14}CO_2$, and contained <1% of the added counts in the particulate fraction. Extended incubation of the CF-degrading strains did not result in a decrease in activity in the particulate fraction, suggesting that the radioactivity was irreversibly bound to cellular components. These results clearly demonstrate that bacteria that produce aromatic oxygenases are capable of converting saturated halocarbons to innocuous products such as $CO_2$.

Example 5

Method for Isolating Naturally-Occurring Strains

This example is illustrative of a method which may be used to isolate naturally-occurring bacterial strains which may contain aromatic oxygenase genes.

In brief outline, the procedure employed was as follows. Approximately 1 gm of hydrocarbon-contaminated soil was placed in an Erlenmeyer flask with 100 ml of basal salts medium "BSM" comprising 4.25 g of $K_2HPO_4 \cdot 3H_2O$, 1 g of $NaHPO_4 \cdot H_2O$, 0.5 g of $NH_4Cl$, 0.123 g of nitrilotriacetic acid, 0.2 g of $MgSO_4 \cdot 7H_2O$, 12 mg $FeSO_4 \cdot 7H_2O$, 2.5 mg $MnSO_4 \cdot H_2O$, 2.5 m $ZnSO_4 \cdot 7H_2O$, and 1 mg $CoCl \cdot 6H_2O$ in 1 liter of water and adjusted to pH 7.0 with either HCL or NaOH. Toluene was added to the flask in the vapor phase by using a small test tube of toluene suspended within the larger flask.

An increase in turbidity, as observed visually or by using a spectrophotometer (Spectronic 20, Bausch & Lomb) at a wave length of 550 nm, was observed within 2 to 7 days of incubation. After the turbidity of the culture increased, a small portion of the culture was added to a new flask of fresh BSM media provided with a source of toluene in the vapor phase.

After the turbidity of this second enrichment culture increased, subsamples of the culture were placed into flasks of fresh BSM media containing intermediates of different toluene oxidation pathways. There are four different toluene oxidation pathways referred to as the T2MO, T3MO, T4MO and TOL plasmid pathways. The intermediates used to identify which of these four pathways is used by a microorganism are o-cresol for the T2MO pathway, m-cresol for the T3MO pathway, p-cresol for the T4MO pathway, and catechol for the TOL plasmid pathway. To isolate useful strains for the present invention, p-cresol (20 $\mu$M) was used to isolate strains producing toluene 4-monooxygenase enzymes, and o-cresol (20 $\mu$M) was used to isolate strains producing toluene 2-monooxygenase enzymes. Cultures growing on cresol were diluted and plated onto agar plates made from BSM containing either p-cresol or o-cresol. Individual bacterial colonies growing on the cresol plates were re-streaked on fresh cresol plates to insure culture purity.

Strain ENVPC5 grew on p-cresol as a sole source of carbon and energy, and strain ENVBF1 and ENV113 grew on o-cresol. All three strains were gram negative rod shaped bacteria, and were identified by fatty acid analysis to be strains of the genus Pseudomonas. For the protocols used in the fatty acid analysis, see FEMS Microbiology Ecology 102:75–84 (1993); Clinical Microbiology Reviews 4:422–438 (1991); J. of Applied Bacteriology, 72:15–321 (1992)).

Example 6

This example illustrates that a variety of aromatic oxygenase-producing bacteria, even those producing different types of aromatic oxygenase enzymes, can oxidize saturated halocarbon compounds.

Aromatic oxygenase-producing strains were obtained from various culture collections. *Burkhoderia cepacia* G4, which produces a toluene 2-monooxygenase ("T2MO"), was obtained from the U.S. EPA Gulf Breeze Laboratory (Gulf Breeze. Fla.). (Shields, M. S., et al., 1989. *Appl. Environ. Microbiol.* 55:1624–1629.) *Pseudomonas mendocina* KR1, ATCC 55706, which produces a toluene 4-monooxygenase ("T4MO"), was obtained from Amgen, Inc. (Palo Alto, Calif.), and *Pseudomonas putida* F1, which produces a toluene dioxygenase ("TDO"), was obtained from Dr. Gerben Zylstra of Rutgers University (New Brunswick, N.J.). (Whited, G. M., and D. T. Gibson. 1991. *J. Bacteriol.* 173:3017–3020; Wackett, L. P., and D. T. Gibson. 1988. *Appl. Environ. Microbiol.* 54:1703–1708.) *Pseudomonas picketti* PKO1, which produces a toluene 3-monooxygenase ("T3MO"), was obtained from Dr. Ronald Olsen, University of Michigan (Ann Arbor, Mich.). (Olsen, R. H. et al., 1994. *J. Bacteriol.* 176: 3749–3756.) All of the toluene oxidizing strains were grown in BSM media with toluene (vapor phase) or sodium glutamate (4 g/L) as a carbon source. To grow cells on toluene vapors, the cells were suspended in 200 ml of BSM medium in a 500 ml Erlenmeyer flask. Toluene (1 ml) was added to a plastic 1.5 ml microcentrifuge tube ("Eppendorf tube") that possessed a plastic cap that had been punctured with a hot 18 gauge needle. The toluene-filled tube was then suspended on a string within the Erlenmeyer flask, and the flask was sealed with a silicone stopper. Toluene that vaporized from the punctured tube served as a growth substrate for the toluene-oxidizing bacteria in the culture liquid. Alternatively, sodium glutamate (4 g/l) was added to the BSM medium as a growth substrate prior to autoclaving.

Several strains of *Escherichia coli* were also used in this study. *E. coli* DH5α, *E. coli* DH10B (Gibco BRL, Gaithersburg, Md.) and *E. coli* JM109 were maintained on LB broth or LB agar (Difco; Detroit, Mich.)—supplemented with ampicillin (100 $\mu$g/ml) if carrying a pUC18Not-derived plasmid or tetracycline (10 $\mu$g/ml) if carrying a pVLT31-derived plasmid. (Yanisch-Perron, C. et al., 1985. *Gene* 33:103–119; Herrero, M., et al., 1990. *J. Bacteriol.* 172:6557–6567; De Lorenzo, V. et al., 1993. *Gene* 123:17–24.)

To elucidate possible aromatic oxidation pathways in the test strains, a series of oxygen utilization experiments was performed essentially as previously described in the literature. (Haigler, B. E., et al., 1992. *Appl. Environ. Microbiol.* 58:2237–2244.) Cultures of *P. mendocina* KR1, *P. putida* F1, *B. cepacia* G4, *P. picketti* PKO1, Pseudomonas sp. strain ENVPC5, Pseudomonas sp. strain ENV113, and Pseudomonas sp. strain ENVBF1 were grown overnight in BSM on toluene vapors. The cells were collected by centrifugation, washed with BSM, suspended in BSM to an optical density at 550 nm ($OD_{550}$) of 1, and placed on ice prior to use. Two-ml subsamples of the cultures were then added to the reaction vessel of a Rank Brothers oxygen probe (Rank Bros. Ltd., Cambridge, England) which was maintained at 30° C. Following a 5 minute temperature equilibration period, either toluene, o-cresol, p-cresol, m-cresol, p-hydroxybenzoate, or catechol was added in 10 $\mu$l dimethyl formamide ("DMF") to a final concentration of 2 mM, and the change in $O_2$ consumption rate was measured by subtracting the basal oxygen consumption rate (i.e., prior to substrate addition) from the oxygen consumption rate observed after addition of the substrate, both rates being measured with a conventional oxygen probe that outputs to a strip chart recorder.

The oxygen consumption rates of toluene-grown cells after exposure to intermediates of the T2MO (o-cresol), T3MO (m-cresol), T4MO (p-cresol), and the TOL plasmid (catechol) pathways are presented in Table 4.

TABLE 4

Substrate-specific oxygen consumption by toluene-grown organisms

| Organism | Oxygen consumption rate μmol O₂/min/mg protein | | | | | |
|---|---|---|---|---|---|---|
| | o-cresol | m-cresol | p-cresol | catechol | toluene | p-hydroxy-benzoate |
| P. mendocina KR1 | 0 | 5.6 | 17 | 0.0 | 9 | 4.7 |
| Strain ENVPC5 | 0 | 8.3 | 9.5 | 0.0 | nd | 2.8 |
| P. putida F1 | 1.3 | 6.6 | 0.0 | 2.1 | 21 | nd |
| Strain ENVBF1 | 7.6 | 0.8 | 0.0 | 4.3 | 15 | 0.0 |
| B. cepacia G4 | 8.3 | 0.72 | 4.3 | 13 | 4 | 0.0 |
| P. picketti PKO1 | 4.9 | 4.9 | 4.2 | 11 | 6.7 | 0.0 | nd = not determined

Both P. mendocina KR1 and Pseudomonas sp. Strain ENVPC5 exhibited the highest rates of oxygen uptake after exposure to p-cresol, and were able to grow with p-cresol as a sole carbon source. They were not able to grow on m-cresol or o-cresol. These results suggest that they produce a toluene-4-monooxygenase. Conversely, Pseudomonas sp. Strain ENVBF1 exhibited its greatest oxygen uptake after exposure to o-cresol, suggesting the production of a toluene-2-monooxygenase, but it grew on all three cresol isomers. Strain ENV113 exhibited virtually the same oxygen uptake pattern as strain G4 (data not shown), which indicated that they each produce a toluene-2-monooxygenase. Strains ENVPC5, ENVBF1, and KR1 produced indigo from indole, whereas strains G4 and ENV113 did not. This test result is of interest because strain G4 does not oxidize indole to produce indigo and does not oxidize CF yet ENVBF1 which, like strain G4, produces a T2MO, oxidizes both CF and indole. These results clearly demonstrate that a variety of aromatic oxygenase-producing bacteria, even those producing different types of aromatic oxygenase enzymes, can oxidize saturated halocarbon compounds.

Example 7

This example is illustrative of a procedure for preparing a recombinant microorganism that can degrade saturated aliphatic halocarbons.

In particular, this example presents a procedure used to introduce the toluene monooxygenase genes from P. mendocina KR1 into E. coli.

This same procedure may be used to prepare other recombinant microorganisms containing the toluene monooxygenase genes or similar genes which encode an aromatic oxygenase capable of degrading saturated aliphatic halocarbons.

Unless otherwise noted, all molecular biological manipulations were performed by methods known to those skilled in the art, essentially as described by Sambrook, et al. (*Molecular Cloning, A laboratory Manual*, 2nd Edition, Cold Spring Harbor Laboratory Press, 1989.) The DNA sequences of tmo A–E and tmo F from P. mendocina KR1 have been reported previously. (Yen, K. -M., et al., 1991. *J. Bacteriol.* 173:5315–5327; Yen, K. M. and M. R. Karl. 1992. *J. Bacteriol.* 174:7253–7261.) Total genomic DNA of P. mendocina KR1 was isolated using the method of Wilson (Wilson, K. 1993. p. 2.4.1–2.4.5. in F. M. Ausubel, et al., (eds.), *Current Protocols in Molecular Biology*. Current Protocols, Brooklyn, N.Y.). The first five genes (tmo A–E) were amplified by using polymerase chain reaction (PCR) with primers TMOU 1 (5'-CGGAATTCTTTAAACCCCACAGGCACGG-3') (SEQ ID NO.:1) and TCED 3 (5'-GCGAATTCGATAATGGTTTGCACTGCCA-3') (SEQ ID NO.:2) which incorporated EcoRI restriction sites on each end of the 3652 bp amplified fragment.

PCR was performed using a GeneAmp kit (Perkin Elmer, Foster City, Calif.) and reaction conditions recommended by the manufacturer. Cycling conditions were: 1 min at 94° C., 30 sec at 50° C., and 3 min at 71° C., for 25 cycles. Amplified DNA was digested with EcoRI (New England Biolabs, Beverly, Mass.), and ligated to similarly digested pUC18Not. The ligation mixture was used to transform E. coli JM109. Clones were selected by plating the cells onto LB agar supplemented with ampicillin (100 μg/ml), and then replica plating onto LB plates that contained 100 μg/ml indole, and 20 μg/ml isopropyl-β-D-thiogalactopyranoside (IPTG). A single colony that formed a blue color from the conversion of indole to indigo, indicating monooxygenase activity, and contained the 3652 bp insert of tmo A–E, as determined by restriction analysis, was selected for further use and designated pRS184. (Ensley, B. D. et al., 1983. *Science* 222:167–169; Yen, K. -M. et al., 1991. 173:5315–5327.)

To add the sixth gene encoding TMO F to the tmoA–E cluster, total chromosomal DNA of P. mendocina KR1 was digested with EcoRV and XmaI and separated on an agarose gel. Fragments ranging from 2 to 3 kb were excised from the gel, purified using the Qiaex system (Qiagen, Chatsworth, Calif.), ligated to similarly digested pRS184, and used to transform E. coli DH5α. Positive clones were selected for their ability to convert indole to indigo, as previously described. Restriction analysis of positive clones confirmed that they contained the 4727 bp tmoA–F insert. The plasmid construct was designated pRS184f. The pRS184f construct was then digested with EcoRI and SmaI and the tmoA–F genes were ligated to similarly digested pVLT31 and used to transform E. coli DH5α, and E. coli DH10B. This plasmid was designated pRS202.

In summary, it can be said that the present invention provides effective and efficient methods and microorganisms for degrading saturated aliphatic halocarbons.

We claim:

1. A method for oxidizing saturated aliphatic halocarbons comprising contacting said halocarbons with an aromatic oxygenase capable of oxidizing said halocarbons, which is produced by a microorganism wherein said saturated halocarbon is selected from the group consisting of chloroform, bromoform, 1,2-dichloroethane, 1,2 dibromoethane, monochloroethane, and monobromoethane.

2. The method of claim 1 wherein said saturated aliphatic halocarbon is chloroform.

3. The method of claim 1 which further comprises providing a co-substrate to support degradation of said halocarbon by said microorganism.

4. The method of claim 3 wherein said co-substrate is selected from the group consisting of toluene, phenol, benzene, ethylbenzene, and xylene.

5. The method of claim 1 wherein said saturated halocarbon is contacted with said microorganism in water.

6. The method of claim 1 wherein said saturated halocarbon is contacted with said microorganism in soil.

7. The method of claim 1 wherein said saturated halocarbon is contacted with said microorganism in vapor phase.

8. The method of claim 1 wherein said saturated halocarbon is contacted with said aromatic oxygenase-producing microorganism within a bioreactor.

9. The method of claim 8 wherein said bioreactor is a fixed film bioreactor.

10. The method of claim 8 wherein said bioreactor is a suspended growth bioreactor.

11. The method of claim 1 wherein said saturated halocarbon is contacted with said aromatic oxygenase-producing bacteria in situ.

12. The method of claim 11 wherein said saturated halocarbon is present in soil or sludge.

13. The method of claim 11 wherein said saturated halocarbon is present in groundwater.

14. The method of claim 1 wherein said aromatic oxygenase is a toluene monooxygenase.

15. The method of claim 1 wherein said aromatic oxygenase-producing microorganism is selected from the group consisting of *Pseudomonas mendocina* KR1, ATCC 55706; Strain ENVPC5; and Strain ENVBF1 ATCC 55819.

16. The method of claim 1 wherein said aromatic oxygenase-producing microorganism is a recombinant microorganism consisting of a host microorganism containing cloned aromatic oxygenase genes.

17. A method for oxidizing saturated aliphatic halocarbons comprising contacting said halocarbons with an aromatic oxygenase capable of oxidizing said halocarbons, which is produced by an aerobic bacteria wherein said saturated halocarbon is selected from the group consisting of chloroform, bromoform, 1,2-dichloroethane, 1,2 dibromoethane, monochloroethane, and monobromoethane.

18. A method for oxidizing saturated aliphatic halocarbons comprising contacting said halocarbons with a toluene-4-monooxygenase which is produced by an aerobic bacteria.

* * * * *

SEQUENCE LISTING (1) GENERAL INFORMATION:

(iii) NUMBER OF SEQUENCES: 2

(2) INFORMATION FOR SEQ ID NO: 1:

```
        (i) SEQUENCE CHARACTERISTICS:
            (A) LENGTH: 28
            (B) TYPE: Nucleic acid
            (C) STRANDEDNESS: single stranded
            (D) TOPOLOGY: Linear (xi) SEQUENCE DESCRIPTION: SEQ ID NO: 1:

CGGAATTCTT TAAACCCCAC AGGCACGG                                              28

(2) INFORMATION FOR SEQ ID NO: 2:

(i) SEQUENCE CHARACTERISTICS:
            (A) LENGTH: 28
            (B) TYPE: Nucleic acid
            (C) STRANDEDNESS: single stranded
            (D) TOPOLOGY: Linear (xi) SEQUENCE DESCRIPTION: SEQ ID NO: 2:

GCGAATTCGA TAATGGTTTG CACTGCCA                                              28
```